United States Patent [19]

Pinto

[11] 4,072,625

[45] Feb. 7, 1978

[54] STEAM-HYDROCARBON PROCESS

[75] Inventor: Alwyn Pinto, Stockton-on-Tees, England

[73] Assignee: Imperial Chemical Industries Limited, London, England

[21] Appl. No.: 659,630

[22] Filed: Feb. 20, 1976

[30] Foreign Application Priority Data

Mar. 3, 1975 United Kingdom ............... 8732/75
Apr. 9, 1975 United Kingdom ............. 14553/75

[51] Int. Cl.² .............................................. C01B 2/16
[52] U.S. Cl. .................. 252/373; 48/196 A; 48/214 A
[58] Field of Search .............. 48/214 A, 196 A; 252/373

[56] References Cited

U.S. PATENT DOCUMENTS

| 2,870,096 | 1/1959 | Baumann | 252/373 |
|---|---|---|---|
| 3,088,919 | 5/1963 | Brown et al. | 252/373 |
| 3,136,624 | 6/1964 | Made et al. | 252/373 |
| 3,150,931 | 9/1964 | Frank | 252/373 |
| 3,441,393 | 4/1969 | Finneran et al. | 48/196 A |
| 3,743,488 | 7/1973 | Bogart | 48/214 A |
| 3,898,057 | 8/1975 | Moller | 48/214 A |

FOREIGN PATENT DOCUMENTS 1,314,984  4/1973  United Kingdom.

OTHER PUBLICATIONS

"Heat Recovery in Ammonia Plants," Silberring, pp. 74-76, CPE Heat Transfer Survey, 1969.
"Operating Performance of 57-3 on the ICI 100 Atmospheres Methanol Plant," Cornell, ICI Catalyst Customers Conf. 1975.

Primary Examiner—Robert L. Lindsay, Jr.
Assistant Examiner—Peter F. Kratz
Attorney, Agent, or Firm—Cushman, Darby & Cushman

[57] ABSTRACT

In a process of reacting a hydrocarbon with steam and-/or carbon dioxide in a reaction zone heated by a combustion furnace to give olefins or process gas containing carbon oxides and hydrogen high grade heat is recovered from furnace flue gases and/or process gas whereby to cool such gases to 150–300° C. When the process gas is used in a synthesis of for example methanol or ammonia, gases at 150°–300° C are also produced. Previously the recovery of heat from such low grade heat sources has been inefficient or inconvenient. According to the invention the heat is recovered by means of an intermediary liquid coolant, which is brought into direct heat exchange with streams to be used in the process. Preferably the liquid is water under pressure and is brought into direct heat exchange with a gas to be fed to the process; by this means 10–30% of the steam can be provided from low grade waste heat.

8 Claims, 1 Drawing Figure

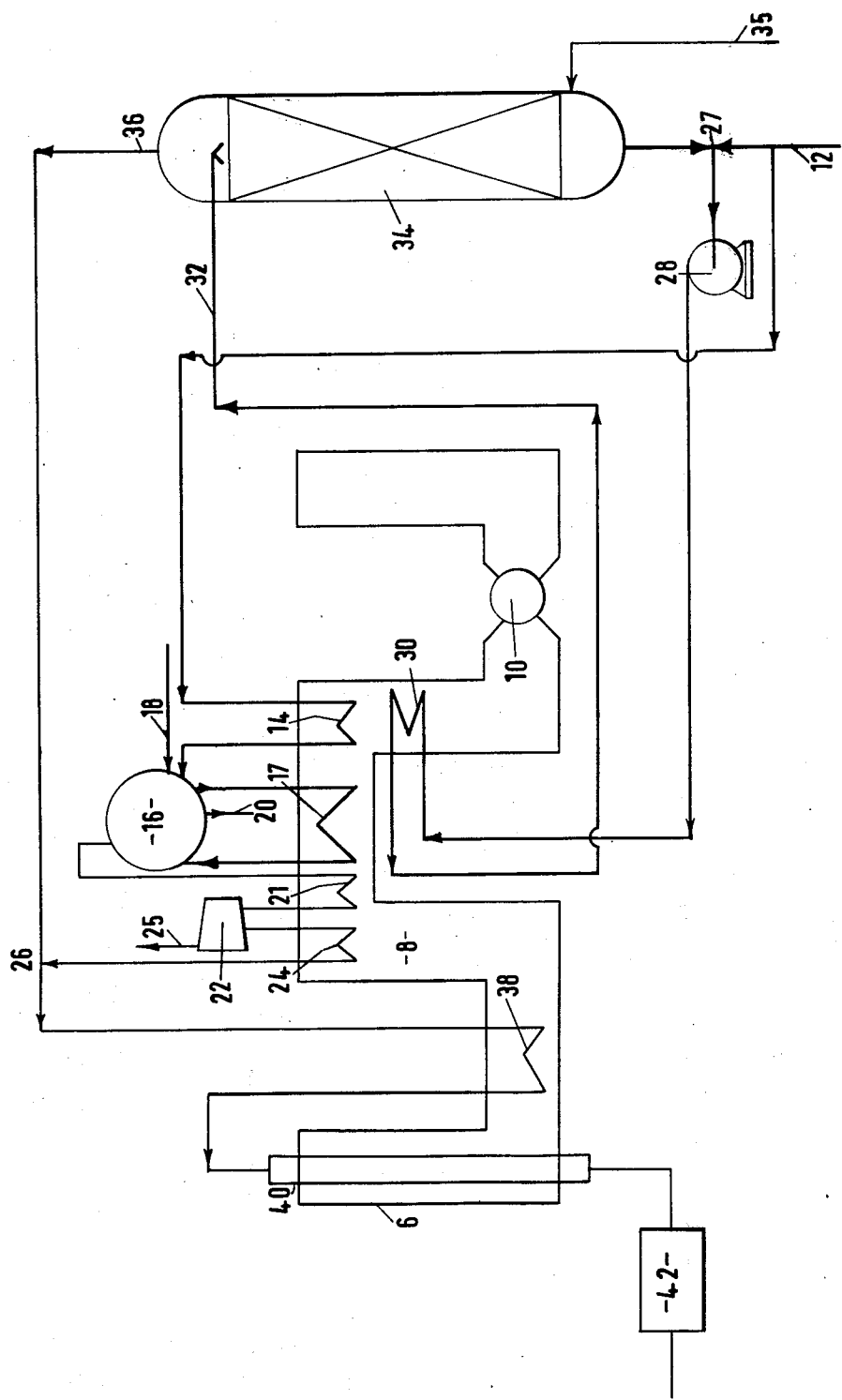

STEAM-HYDROCARBON PROCESS

This invention relates to a process and apparatus for treating hydrocarbons with steam and/or carbon dioxide.

In important processes for treating hydrocarbons a reaction mixture containing hydrocarbons and steam and/or carbon dioxide is heated in tubes suspended in a furnace. The furnace combustion gases and the process gas stream produced are at a high temperature, such that it is necessary and practicable to recover heat from them. Consequently it has become customary to bring the combustion gases and/or process gas stream into heat exchange in waste-heat boilers, boiler feed water heaters and gas heaters. Such heat exchanges lower the temperature usually to 300° C, possibly to about 250° C, but further heat recovery becomes less and less readily practicable owing to the low temperature and to the distance of the further heat exchangers from the process or furnace feed inlets where the most important heat-absorbing streams occur. It has been proposed to recover heat from the lowest temperature combustion gases by preheating furnace combustion air, but the necessary long wide-bore insulated duct and large blower involve high capital and operating costs.

A similar problem arises in the recovery of heat from gas streams produced by any further reactions carried out such as the shift reaction and synthesis reactions, when such streams are at 300° C or less, so that high grade heat cannot be recovered from them.

We have now realised that such heat recoveries can be made more efficiently by using an intermediary liquid coolant to transfer the heat from low-grade sources at 150°–300° C since high heat transfer coefficient with gaseous streams are obtained in the heat exchangers, and the transport of the liquid from distant sections of the plant involves relatively inexpensive pipework and pumps. In particular, when the coolant is liquid water under pressure and the resulting hot water is allowed to evaporate in the presence of a gaseous stream being fed to the process, a useful proportion (for example 10 to 30%) of the steam required for the treatment can be provided, which would otherwise have been supplied from higher grade heat recoveries.

According to the invention a process of treating hydrocarbons comprises:

(a) reacting a hydrocarbon with steam and/or carbon dioxide endothermically at an elevated temperature in a reaction zone heated by a combustion furnace, to give a process gas stream;

(b) providing, by cooling the combustion gases discharged from the said furnace, and/or by cooling the process gas stream before or after a shift reaction, and/or by a synthesis reaction of the process gas stream, at least one gas stream having a temperature in the range 150°–300° C;

(c) exchanging heat contained in at least one of the said gas streams at 150°–300° C with a liquid coolant whereby to produce at least one hot liquid stream; and (d) one or both of the following further heat exchanges, namely (i) when the liquid stream is hot water under pressure, bringing it into direct heat exchange with at least one gaseous stream about to be fed to step (a), whereby to provide a part of the steam feed to step (a); and (ii) bringing at least one such hot liquid stream into indirect heat exchange with a gas or liquid stream to be used in the process or furnace.

The invention provides also such a process in combination with the steps required to convert the process gas stream to various products, as detailed below, and also apparatus for carrying out the hydrocarbon treatment without or with the further steps.

Hydrocarbon treatments according to the invention include pyrolysis to produce a process gas stream rich in olefins, in which event either no catalyst or a catalyst free of hydrogenating components is present in the heated reaction zone. For the application of the invention a more important treatment is in the presence of a catalyst containing a hydrogenating component, to give a process gas stream containing hydrogen and carbon oxides. Such a hydrogen-containing process gas stream may be for example a crude synthesis gas to be treated further so as to be suitable for the synthesis of products such as ammonia, methanol, liquid hydrocarbons, oxygenated hydrocarbons or substitute natural gas. Alternatively it may be a crude stream to be treated so as to consist substantially of hydrogen. In a further process the gas may be a metallurgical reducing gas or a stream to be treated to give such a gas. The further treatments of such streams are discussed further below.

The hydrocarbon may be normally gaseous or normally liquid. Methane and gaseous hydrocarbons are especially suitable, except that methane is of course not the sole hydrocarbon used when the crude gas is to be converted to substitute natural gas.

The proportions of steam and carbon dioxide relative to hydrocarbon and to each other depend on the purpose for which the hydrogen-containing gas is required. Typical proportions, expressed as molecules of steam plus carbon dioxide per atom of carbon in the hydrocarbon are 1.2 to 2.0 for making metallurgical reducing gas, 2.0 to 4.0 for making town gas, 2.5 to 5.0 for making ammonia synthesis gas and 2.0 to 7.0 for making hydrogen or synthesis gas for methanol, liquid hydrocarbons or oxygenated hydrocarbons. The use of steam without carbon dioxide is convenient for all these purposes except synthesis of liquid hydrocarbons or oxygenated hydrocarbons, for which hydrogen and carbon monoxide in the ratio between about 1:1 and 2:1 are required. For methanol synthesis, although the stoichiometric requirement is 2 molecules of hydrogen per molecule of carbon monoxide (corresponding to 3 per molecule of carbon dioxide), it is customary to use steam without carbon dioxide, rather than incur the expense of providing the carbon dioxide.

The temperature at the outlet of step (a) is typically in the range 600°–1100° C, depending on the intended use of the gas. Thus it may be for example 700°–900° C for the synthesis gases or town gas or hydrogen intermediate gas or 900°–1100° C for metallurgical reducing gas. The inlet temperature is typically in the range 300°–600° C but may be up to 700° C if the starting hydrocarbon is methane.

The pressure is typically in the range 1–50 ata and especially over 10 ata, for example 15–40 ata in making ammonia synthesis gas or town gas, or for example 10–30 ata in making methanol synthesis gas or hydrogen; for other uses lower pressures are typical, for example 1–5 ata in making reducing gas and 5–25 ata in making olefins. When, as in the synthesis of ammonia or methanol or liquid hydrocarbons or oxygenated hydrocarbons, the gas produced by the process has to be compressed, the energy required to drive the compressor is preferably derived, directly or via electricity, from high pressure steam (over 50 ata, for example 60–120 ata) generated in the course of step (b) in one or more waste heat boilers heated by furnace combustion gases and/or by process gas and/or reacted synthesis gas, and let down in pass-out turbines exhausting at the pressure required at the inlet of step (a).

The catalyst for making hydrogen-containing process gas typically is a steam reforming catalyst comprising 5–50% (calculated as NiO) of nickel supported on a refractory oxide or oxide mixture, but other catalysts containing cobalt or a platinum group metal instead of or in addition to nickel have been proposed. The refractory component commonly contains alumina, magnesia, silica, titania or zirconia alone or in mixtures or compounds with each other or with calcium oxide, for example as spinels or hydraulic cements. If the hydrocarbon or the process conditions are such as to produce by-product carbon using a catalyst intended primarily for the methane/steam reaction, a modified catalyst containing an alkali metal compound can be used for at least the inlet portion of the catalyst bed. Such a carbon problem can be solved for some hydrocarbon feeds by suitably designing the heat-flow characteristics of the furnace, including possibly the use of process air or oxygen, or arranging for the hydrocarbon to be substantially reacted initially at under 600° C.

The furnace (a "steam reforming furnace") to be used in making hydrogen-containing process gas comprises a refractory lined box in which are suspended catalyst-containing tubes of internal diameter usually 3–6 inches. The tubes are heated by burners disposed usually at the top or sides of the box. The combustion gases from the burners are usually vented from the top of the box if the burners are at the sides or from the bottom if the burners are at the top. After leaving the box the gases pass through the combustion gas duct over banks of tubes through which are circulated various process feed streams including, in particular (in descending order of heat recovery grade) reactants fed to step (a), steam to be superheated, the water of the boiler providing high pressure steam for driving turbines and providing steam to be fed to step (a), feed water for the boiler, hydrocarbon process feed, furnace fuel and furnace combustion air. If the gas is to be used for ammonia synthesis there is commonly an air heater feeding a secondary reformer. There may be a carbon dioxide heater or synthesis purge gas heater. The duct may be provided with auxiliary fuel burners to provide heat for raising steam at start-up or when by accident or design the furnace combustion gases provide insufficient steam.

Whereas previously the preheating of furnace combustion air has been carried out in a gas/gas heat exchanger in the flue gas duct, in the process of the invention the furnace burners can be fed with air at ambient temperature or with air heated by indirect heat exchange with hot liquid from step (d ii). Alternatively, a gas turbine can be used to provide rotary power, for example for synthesis gas compression or for electricity generation, and its hot effluent used as furnace combustion air.

Similar principles apply to the rather different furnaces that have been developed for treating hydrocarbons to produce olefins.

The process gas stream, except when it is immediately to be used as metallurgical reducing gas, is cooled from the above-mentioned outlet temperature in a manner similar to the combustion gases. If the gas is to be used for olefin production or for the synthesis of methanol or liquid hydrocarbons or oxygenated hydrocarbons, cooling to such a low temperature that the excess steam in the gas condenses and can be separated is normally carried out before any further chemical reactions; the heat exchange with liquid conveniently follows higher grade heat recoveries including steam generation and boiler feed water heating but precedes final cooling to the steam dewpoint. If the gas is to be used for ammonia synthesis or for making hydrogen, cooling is at first to the inlet temperature of the carbon monoxide shift reaction, namely 180°–270° C for a "low temperature" shift or 350°–450° C for a "high temperature" shift reaction. The shift reaction is exothermic and accordingly the gas leaving the high temperature reaction can be cooled by indirect heat exchange with recovery of high grade heat, as high pressure steam and/or boiler feed water. In a widely used process a high temperature shift reaction is followed by a low temperature shift reaction and such heat recoveries provide the necessary intermediate cooling. Heat exchange (conveniently indirect) with liquid according to step (c) may be carried out as part of such inter-stage heat recovery and is also a very useful way of recovering useful heat from the gas produced by the low temperature shift reaction. After the low temperature shift reaction substantially the whole carbon content of the gas is in the form of carbon dioxide, and this is washed out by means of a regenerable absorbent such as potassium carbonate solution or an alkanolamine or a physical absorbent such as "Sulfinol" or an ester. Residual carbon oxides are then catalytically converted to methane; this is an exothermic but the quantities of reactant involved are usually too small to make recovery of heat practicable.

When in step (c) the gas stream at 150°–300° C contains steam but substantially no constituents more water-soluble than carbon dioxide, and is at superatmospheric pressure, the heat exchange to cool it can be carried out with liquid water directly insteam of indirectly. By this means a substantial part of the steam is condensed and less need be removed by indirect cooling. The apparatus required for such direct heat exchange is of simple construction.

The gas stream from which steam is removed in this way may be for example gas to be treated for olefin separation, synthesis gas for methanol or liquid hydrocarbons or oxygenated hydrocarbons, or gas that has undergone a shift reaction as a stage in the production of ammonia synthesis gas or a hydrogen stream.

The pressure and steam content of the gas stream should be high enough to cause steam to condense into the water and preferably are high enough to produce a hot water stream at 150°–300° C. If the pressure and/or steam content are not high enough to produce such a hot water stream, the heat exchange is still of value in pre-heating water to be subjected to indirect heat exchange in the process.

The main constituents of the gas stream are normally one or more of hydrogen, carbon monoxide, carbon dioxide, nitrogen and methane. All of these except carbon dioxide are substantially insoluble in water. If the pressure and temperature are such that carbon dioxide is significantly dissolved, it will eventually be fed to the steam/hydrocarbon reaction (a), in which it normally has no ill effect; precautions should, however, be taken if the concentration of dissolved carbon dioxide is sufficient to cause corrosion. There may be trace quantities of methanol if the gas stream is the effluent of a copper-containing low temperature shift catalyst, but this will be reacted without difficulty in step (a). There may be traces of ammonia if the gas contains nitrogen and has been shifted over an iron oxide containing catalyst; this also reacts in step (a) without difficulty.

The direct heat exchange cooling the steam-containing gas stream may be carried out in two or more stages, analogously to the direct heat exchange of step (d i). After the direct heat exchange to produce the hot water stream, final cooling and water separation is normally needed, especially if the gas is to be compressed or subjected to low temperature separation.

For step (d ii) the liquid coolant may be for example a diphenyl-diphenyl ether mixture or a molten alloy but is conveniently liquid water under pressure, especially if both heat exchanges are used, since then a common pressurized hot water system for the whole plant can be operated.

The heat recoveries from reacted synthesis gas are, owing to the solubility of methanol and ammonia in water, carried out by indirect heat exchange if water is used as the coolant.

In the synthesis of methanol by one of the newer low-temperature processes the reacted gas is commonly at under 300° C, such that heat can be recovered from it as in step (c). Conveniently the reacted gas stream is divided into two partstreams, one of which is heat-exchanged with cool synthesis gas to bring it to synthesis inlet temperature, and the other of which is heat-exchanged with the water.

If the gas is used for methanol synthesis by the older process with reacted gas temperatures in the range 350°–450° C or for ammonia synthesis in which the reacted gas temperature is usually in the range 480°–530° C, a high grade heat recovery, producing steam or boiler feed water, is preferably carried out before water-heating as in step (c). Alternatively step (c) can be effected by reacted gas that has been cooled by heat exchange with incoming cool synthesis gas.

The temperatures of reacted gases in other synthesis reactions range from about 150° C to about 550° C, or up to 850° C in methane-synthesis. The choice of gas stream for liquid-heating follows the principles already illustrated.

The temperature of the hot liquid stream is suitably in the range 150° to 300° C. The temperature of the gas after heat exchange with the liquid is suitably in the range 100° to 150° C; a further recovery of heat is possible by heat exchange between such cooled gas and one or more of the gaseous streams, so that such streams are warmed before coming into the direct heat exchange with the hot liquid.

The stream brought into heat exchange with the hot liquid is suitably a gaseous hydrocarbon, especially if the liquid is water under pressure and direct heat exchange is used. If desired it could be a carbon dioxide stream or possibly a synthesis purge gas stream being recycled to the hydrocarbon-steam reaction step (a). The gaseous stream is conveniently at ambient temperature but may have been preheated for example by warming as described in the preceding paragraph; if it is preheated, this should of course not be by heat exchange with a gas stream upstream of the liquid heater since thereby degradation of higher grade heat would take place. If the hydrocarbon feed to step (a) is normally liquid it is preferably vaporised before the direct heat exchange with hot water. For such preheating or vaporisation heat can be derived from one or more of the gas streams not being used for heating the liquid in step (c). The streams mentioned in this paragraph are very suitably heated by direct heat exchange with the hot water. If indirect heat exchange is employed, then other streams, for example, air or carbon dioxide removal solution can be heated in step (d ii).

The direct heat exchange in step (d i) is preferably carried out in more than one stage, each fed with hot water, because the extent of transfer of heat and steam to the gas is limited by the temperature fall due to the latent heat of the water. The hot water stream may be the same for each stage but preferably hotter water is used for each subsequent stage. The hot water stream may have been heated by the same or by different gas streams.

After the direct heat exchange the steam-containing gas to be fed to step (a) is further heated by indirect heat exchange suitably with furnace combustion gases or process gas, to suitably 350° to 600° C, before or after mixing with the other ingredients of step (a).

The process of the invention is advantageously applied to the production of methanol by reacting one or more carbon oxides with hydrogen at a temperature of 160°–300° C over a catalyst containing copper. Although such a process has become well established, it has been recognised that the synthesis temperature is too low to permit heat to be recovered as steam at a pressure high enough to be used in pass-out turbines exhausting at above the inlet pressure of the synthesis gas generation process. Consequently all the steam required for such turbines must be raised in the synthesis gas generation section. By the process of the invention it is possible to provide from a low grade heat source 10 to 30% of the steam required for synthesis gas generation. This enables the total process to be redesigned by, for example, (i) increasing the steam to carbon ratio in synthesis gas generation and thus decreasing the methane content of the synthesis gas and decreasing compression and circulation energy consumption and cost; and/or (ii) lowering the temperature of synthesis gas generation and thus burning less fuel in the furnace; and/or (iii) diverting steam from turbines exhausting at high pressure into the synthesis gas generation process to turbines exhausting at low pressure into the methanol distillation section; and/or (v) decreasing or dispensing with auxiliary firing in the flue gas duct. Over-all a decrease in energy consumption of about 2 to 5% can be achieved.

Similar contributions to steam requirements and to energy economy are possible in other applications of the invention.

The drawing shows a flowsheet of a preferred process and apparatus in which combustion gases are cooled by indirect heat exchange and steam is introduced by direct heat exchange, in a form suitable for making a crude methanol synthesis gas from natural gas.

The process is based on steam reforming furnace 6, heated by burners not shown, the combustion gases from which are drawn into duct 8, (which contains auxiliary burners) by induced-draught fan 10 and then discharged to atmosphere via a stack. In duct 8 heat is recovered from the combustion gases in various heat exchangers, of which those relevant to the invention will be described.

The characteristic feature of the process is the manner by which water is fed. Water enters the process at 12 and is divided into two streams. The major stream is heated to generate steam for driving turbines and to supply process requirements. This stream passes through boiler feed water heater 14 and then into drum 16 from which water is circulated via boiler 17 to generate steam. Drum 16 may also receive feeds of water indicated generally by 18 from other heat recoveries, for example boiling water from a waste heat boiler in the crude product gas heat recovery 42, or boiler feed water from lower-grade heat recoveries such as the crude gas downstream of such a waste heat boiler or from heat exchange with gas leaving the methanol synthesis catalyst, if the methanol synthesis is at under 300° C. The return water line to such waste heat boilers is indicated generally at 20. Steam from drum 16 passes through superheater 21 and power recovery turbines indicated generally by 22. Part of the exhaust from the turbines is taken off at an intermediate pressure, reheated by combustion gases at 24 and fed to the reactant stream at 26. The remainder of the effluent is taken off at 25 at a low pressure, for uses such as the re-boiler of a methanol distillation column, or for condensation and possibly recycle into the process at 12.

The minor water stream is united at 27 with a recycle water stream and fed by means of pump 28 to water heater 30, which is in the hot combustion gas duct 8 downstream of heat exchangers 38, 24, 17 and 14. It then passes via pipe 32 t0 humidifier 34 in which it trickles down over bubble-trays or particulate packing, in contact with a rising current of natural gas 35, into which it evaporates incompletely. Water that has not evaporated leaves the bottom of humidifier 34 as the recycle stream to be united with the minor water stream at 27. (The natural gas at 35 could be preheated by heat exchange with combustion gases downstream of water-heater 30).

The water-saturated natural gas leaves humidifier 34 at 36 and is united with the vaporised major water stream at 26 to give the steam reforming reaction mixture, which is then preheated by the hottest combustion gases at 38 and fed to catalyst-filled tube 40 heated in furnace 6. The gas leaving tube 40 is fed to the crude product gas heat recovery system indicated generally by 42, which commonly includes a waste heat boiler, a boiler feed water heater and lower grade heat exchangers.

In alternative forms of the invention water-heater 30 can be part of heat recovery system 42, disposed downstream of a waste heat boiler and boiler feed water heater. In a further alternative from water heater 30 can be heated by gas leaving the methanol synthesis catalyst, possibly downstream of heat exchange with unreacted synthesis gas or boiler feed water. In still a further alternative such crude synthesis gas or reacted synthesis gas can be brought into heat exchange with natural gas to be fed at 35.

It will be appreciated that minor heat exchanges, such as a low grade boiler feed water heater between points 12 and 14, a gas preheater between points 36 and 26, and the water heaters used in demineralising and de-aerating the water fed at 12, have been omitted for the sake of clarity.

EXAMPLE 1

Combustion Gases Cooled by Indirect Heat Exchange; Steam Introduced by Direct Heat Exchange The synthesis gas generation section of a process designed to produce 2000 metric tons per day of methanol is fed with 2650 kg mol/hour of desulphurised natural gas, calculated as methane, and 7950 kg mol/hour of steam at 18.3 ata pressure. This mixture is reacted over a nickel-alumina-aluminous cement catalyst at 850° C outlet temperature in 4 inch internal diameter tubes suspended in a steam reforming furnace to give a gas containing hydrogen, carbon monoxide, carbon dioxide and excess steam, whereafter this gas is cooled in stages until the water condenses. After separation of the water the gas is compressed to 100 ata, mixed with recycled reacted gas from which methanol has been separated and fed to a methanol synthesis catalyst. Of the steam fed to the generation section, 6629 kg mol/hour are derived from the exhaust of pass-out turbines by steam raised at 110 ata in waste heat boilers in the combystion gas duct of the furnace and in the process gas after leaving the catalyst, that is, from high-grade heat recovery. The remaining 1321 kg mol/hour are provided by injecting into the natural gas feed (initially at 30° C) at the rate of 222 metric tons per hour a stream of water heated to 220° C in a heat exchanger in the furnace combustion gases duct at a level at which the gas temperature is at 270° C following abstraction of higher grade heat by the waste heat boiler and a boiler feed water heater. By thus heating water the combustion gases are cooled to 130° C, whereafter they are discharged to atmosphere. The temperature of the water-saturated natural gas is 170° C. The temperature of the water (198.2 metric tons per hour) remaining after contact with the natural gas is 95° C; this water is mixed with fresh water at 95° C as supplied from process condensate and from a demineralisation and deaeration plant, and the mixture recycled to the water heater.

The heat load of the water-heater is 27720 tonne-calories per hour, the same as that of a furnace combustion air preheater, if one were used. This heat is fed to the process internally instead of via the furnace burners. It is also transmitted by means of water pipes and with the aid of water-pumps, which may (unlike a combustion air fan) be duplicated at small expense if provision has to be made against failure. Should the water flow be interrupted, the process can be continued by increasing the steam supply by using the auxiliary burners in the combustion gas duct.

If the process includes preheating of furnace combustion air by means of hot liquid, the plant may include a pump and water heater similar to items 28 and 30 of the drawing but feeding for example the tubes of a finned tube air heater in the furnace combustion air supply duct. Since the water enters only into indirect heat exchange, it remains constant in quantity and thus no make-up water is required for this duty. In the water heater the water can be circulated through externally finned tubes; when both gas-contacting are finned, especially good heat transfer coefficient are attained.

Modification of Flowsheet for Production of Hot Water by Direct Heat Exchange The flowsheet is similar except that indirect heat exchanger item 30 is not used and in its stead a direct heat exchanger forms part of heat recovery section 42. Such a direct heat exchanger is similar in construction to humidifier 34 on the flowsheet, but is operated as follows:

(i) it is fed at a position corresponding to 35 with a steam-containing gas stream;

(ii) it is fed at a position corresponding to 32 with cool water;

(iii) it produces at a position corresponding to 36 a steam-denuded gas stream to be fed to a final water-removal step; and (iv) it produces at a position corresponding to 27 a hot water stream to be used in adding steam to a gas to be fed to the steam hydrocarbon reaction stage.

It will be appreciated that the water leaving pump 28 is the feed to (ii) and the water fed at 32 is the water leaving (iv). In Example 2 the direct heat exchanger forming part of modified heat recovery section 42 is referred to as column A and humidifier 34 as column B.

If desired, water heater 30 and the direct heat exchanger could both be used, feeding a single hot water stream to humidifier 34 or feeding two humidifiers 34 or feeding two humidifiers 34 in series. Other possible combinations are described above.

EXAMPLE 2

Process Gas Cooled by Direct Heat Exchange; Steam Introduced by Direct Heat Exchange In a process designed to produce 1100 metric tons per day of methanol the synthesis gas generation section is fed with 1628 kg mol/hour of desulphurised natural gas, calculated as methane, and 5000 kg mol/hour of steam, the pressure of the mixture at the inlet of the catalyst for the steam/hydrocarbon reaction being 21.4 ata. The mixture is reacted over nickel-alumina-aluminus cement catalyst at 850° C outlet temperature in 4 inch internal diameter tubes suspended in a steam reforming furnace to give a gas containing hydrogen, carbon monoxide, carbon dioxide and excess steam, the steam amounting by the volume to 33% of the gas. The gas is passed through a waste heat boiler raising steam at 110 ata and cooled to 200° in a boiler feed water heater. It is now passed into the bottom of packed column (a) in which it rises through a downward-flowing water stream. The gas leaves the top of column A at 152° C with a steam content of 26% by volume and is passed to an air-cooled indirect cooler and water-separator. The water fed to the top of the column A (4196 kg mol/hour) is initially at 110° C. Together with condensed steam it leaves the bottom of column A at 180° C, the total rate being 86 metric tons per hour (4772 kg mol/hour). This hot water is pumped to the top of packed column (B) down which it flows through a rising stream of natural gas to be fed to steam/hydrocarbon reaction. The natural gas, initially dry and at 30° C, is fed at the rate of 1628 kg mol/hour. It leaves the top of column B mixed with 576 kg mol/hour of steam, the temperature of the mixture being 170° C. The water leaving the bottom of column B is the feed for the top of column A. The natural gas/steam mixture contains 11.5% of the steam fed to the steam/hydrocarbon reaction stage. The remaining part of the steam is derived from the exhaust of pass-out turbines driven by the steam raised at 110 ata in the above-mentioned waste heat boiler and also in a waste-heat boiler in the combustion gas duct of the steam reforming furnace.

I claim:

1. A process of treating hydrocarbons which comprises:
   a. reacting a normally gaseous hydrocarbon with steam endothermically over a catalyst at an outlet temperature in the range 700° to 900° C. in a reaction zone heated by a combustion furnace, to give a process gas stream containing hydrogen, carbon monoxide and carbon dioxide;
   b. recovering heat by cooling the process gas stream resulting from said reaction of a hydrocarbon with steam in heat exchange in a boiler raising steam at the pressure in the range of 60 to 120 ata. and then with feed water for said boiler, until the temperature of said process gas stream has fallen to 150° to 300° C;
   c. transferring heat contained in said process gas stream at 150° to 300° C., to water under pressure; and
   d. bringing the resulting hot water under pressure into direct heat exchange with the normally gaseous hydrocarbon to be reacted in step (a), to provide 10 to 30% of the steam to tbe reacted in step (a).

2. A process according to claim 1 in which step (a) is operated at and a pressure over 10 ata.

3. A process according to claim 2 in which the hydrocarbon fed to step (a) is normally gaseous and liquid water under pressure is brought into direct heat exchange with it in step (d i).

4. A process according to claim 3 in which the direct heat exchange provides 10 to 30% of the steam required.

5. A process of treating hydrocarbons which comprises:
   a. reacting a normally gaseous hydrocarbon with steam endothermically over a catalyst at an outlet temperature in the range 700° to 900° C. in a reaction zone heated by a combustion furnace, to give a process gas stream containing hydrogen, carbon monoxide and carbon dioxide;
   b. recovering heat by cooling the combustion gases discharged from said furnace in heat exchange, in a boiler raising steam at a pressure 60 to 120 ata. and then with feed water for said boiler, until the temperature of the combustion gas has fallen to 150° to 300° C.;
   c. transferring heat contained in said cooled combustion gas at 150 to 300° C. to water under pressure; and
   d. bringing the resulting hot water under pressure into direct heat exchange with the normally gaseous hydrocarbon to be reacted in step (a), to provide 10 to 30% of the steam to be reacted in step (a).

6. A process according to claim 5 in which step (a) is operated at a pressure over 10 ata.

7. A process of treating hydrocarbons which comprises:
   a. reacting a normally gaseous hydrocarbon with steam endothermically over a catalyst at an outlet temperature in the range 700° to 900° C. in a reaction zone heated by a combustion furnace, to give a process gas stream containing hydrogen, carbon monoxide and carbon dioxide;
   b. recovering heat by cooling the combustion gases discharged from said combustion furnace in heat exchange in a boiler raising steam at a pressure in the range of 60 to 120 ata. and then with feed water for said boiler, until the temperature of the combustion gas has fallen to 150° to 300° C.;
   c. transferring heat contained in said cooled combustion gas at 150° to 300° C. to water under pressure; and d. bringing the resulting hot water under pressure into indirect heat exchange with air to be fed to the burners of the combustion furnace in step (a).

8. A process of treating hydrocarbons which comprises:
   a. reacting a normally gaseous hydrocarbon with steam endothermically over a catalyst at an outlet temperature in the range 700° to 900° C. in a reaction zone heated by a combustion furnace, to give a process gas stream containing hydrogen, carbon monoxide and carbon dioxide;
   b. recovering heat by cooling the process gas stream resulting from said reaction of a hydrocarbon with steam in heat exchange in a boiler raising steam at the pressure in the range of 60 to 120 ata. and then with feed water for said boiler, until the temperature of said process gas stream has fallen to 150° to 300° C.;
   c. transferring heat contained in said process gas stream at 150° to 300° C., to water under pressure; and
   d. bringing the resulting hot water under pressure into indirect heat exchange with air to be fed to the burners of the combustion furnace in step (a).

* * * * *